(12) United States Patent
Derry et al.

(10) Patent No.: US 10,800,079 B2
(45) Date of Patent: Oct. 13, 2020

(54) ONE-PIECE SENSOR FOR A BIOELECTRODE AND PROCESSES FOR PRODUCTION

(71) Applicant: 3M INNOVATIVE PROPERTIES COMPANY, Saint Paul, MN (US)

(72) Inventors: Cameron E. Derry, London (CA); John P. Tryphonopoulos, London (CA)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/063,559

(22) PCT Filed: Dec. 29, 2016

(86) PCT No.: PCT/US2016/063956
§ 371 (c)(1),
(2) Date: Jun. 18, 2018

(87) PCT Pub. No.: WO2017/112368
PCT Pub. Date: Jun. 29, 2017

(65) Prior Publication Data
US 2019/0047192 A1 Feb. 14, 2019

Related U.S. Application Data

(60) Provisional application No. 62/270,649, filed on Dec. 22, 2015.

(51) Int. Cl.
*B29C 45/14* (2006.01)
*B29C 45/00* (2006.01)
(Continued)

(52) U.S. Cl.
CPC ...... *B29C 45/14336* (2013.01); *A61B 5/0006* (2013.01); *A61B 5/0408* (2013.01);
(Continued)

(58) Field of Classification Search
CPC .... B29C 45/14344; B29C 2045/14327; B29C 2045/14368; B29C 45/14016;
(Continued)

(56) References Cited

U.S. PATENT DOCUMENTS 3,834,373 A  9/1974 Sato
3,976,055 A  8/1976 Monter
(Continued)

FOREIGN PATENT DOCUMENTS

CA  2585355  10/2005
CN  102303393 A  1/2012
(Continued)

OTHER PUBLICATIONS

Ineos Olefins & Polymers USA, "Polypropylene Processing Guide", Mar. 2007, available online at https://www.ineos.com/globalassets/ineos-group/businesses/ineos-olefins-and-polymers-usa/products/technical-information--patents/ineos_polypropylene_processing_guide.pdf (Year: 2007).*

(Continued)

*Primary Examiner* — Matthew J Daniels
*Assistant Examiner* — Hana C Page (57) ABSTRACT

A process for producing a sensor for a biomedical electrode (e.g. an ECG electrode) involves injection molding an electrically conductive resin through a film of a backing material to form the sensor directly in the backing material and coating the contact face of the sensor with a non-polarizable conductive material (e.g. silver-containing material). Additional steps of applying an electrolyte over the non-polarizable conductive material coated on the contact face and applying a liner over the electrolyte results in the biomedical electrode. Biomedical electrode produced thereby have the sensor secured in a film of the backing material with a contact face of the sensor disposed on a first (Continued)

side of the film and a post of the sensor protruding from a second side of the film opposite the first side. The process permits production of one-piece sensors for bioelectrodes in a continuous fashion without the need for studs to retain sensors in a film of the backing material.

18 Claims, 4 Drawing Sheets

(51) Int. Cl.
*A61B 5/0408* (2006.01)
*A61B 5/00* (2006.01)
*B29K 105/12* (2006.01)
*B29L 31/00* (2006.01)

(52) U.S. Cl.
CPC ...... *A61B 5/04087* (2013.01); *B29C 45/0053* (2013.01); *B29C 45/14344* (2013.01); *A61B 2562/0209* (2013.01); *A61B 2562/125* (2013.01); *B29C 45/14016* (2013.01); *B29C 2045/0079* (2013.01); *B29K 2105/12* (2013.01); *B29K 2995/0005* (2013.01); *B29L 2031/752* (2013.01); *B29L 2031/753* (2013.01)

(58) Field of Classification Search
CPC .......... B29C 45/14336; A61B 5/04087; A61B 5/0416; A61B 5/0408–0424
See application file for complete search history.

(56) References Cited

U.S. PATENT DOCUMENTS

| | | | | |
|---|---|---|---|---|
| 4,107,121 | A * | 8/1978 | Stoy | C08L 33/20 264/182 |
| 4,377,170 | A | 3/1983 | Carim | |
| 4,563,182 | A * | 1/1986 | Stoy | A61F 5/0093 424/436 |
| 4,635,642 | A | 1/1987 | Cartmell | |
| 4,727,881 | A | 3/1988 | Craighead | |
| 4,848,348 | A | 7/1989 | Craighead | |
| 4,938,219 | A | 7/1990 | Ishii | |
| 5,042,144 | A * | 8/1991 | Shimada | A61B 5/04087 156/235 |
| 5,326,272 | A * | 7/1994 | Harhen | A61B 5/0416 439/859 |
| 5,406,945 | A | 4/1995 | Riazzi | |
| 5,489,215 | A | 2/1996 | Wright | |
| 5,782,761 | A | 7/1998 | Gusakov | |
| 6,268,405 | B1 * | 7/2001 | Yao | A61L 27/16 264/28 |
| 6,415,170 | B1 * | 7/2002 | Loutis | A61B 5/04087 600/391 |
| 6,511,701 | B1 | 1/2003 | Divigalpitiya | |
| 6,569,494 | B1 | 5/2003 | Chambers | |
| 6,650,922 | B2 | 11/2003 | Kurata | |
| 6,834,612 | B2 | 12/2004 | Chambers | |
| 6,919,504 | B2 | 7/2005 | McCutcheon | |
| 7,034,403 | B2 | 4/2006 | Divigalpitiya | |
| 8,637,136 | B2 | 1/2014 | Ferguson | |
| 9,192,313 | B1 | 11/2015 | Lisy | |
| 2001/0041933 | A1 * | 11/2001 | Thoma | A61F 2/2445 623/2.36 |
| 2005/0261565 | A1 * | 11/2005 | Lane | A61B 5/04087 600/394 |
| 2007/0093705 | A1 * | 4/2007 | Shin | A61B 5/0416 600/372 |
| 2009/0253975 | A1 | 10/2009 | Tiegs | |
| 2010/0159197 | A1 | 6/2010 | Ferguson | |
| 2013/0037987 | A1 | 2/2013 | Clarke | |
| 2013/0085368 | A1 | 4/2013 | Coggins | |
| 2015/0148646 | A1 * | 5/2015 | Park | A61B 5/04 600/391 |

FOREIGN PATENT DOCUMENTS

| | | |
|---|---|---|
| CN | 203636902 U | 6/2014 |
| EP | 0195859 | 10/1986 |
| EP | 0597156 | 5/1994 |
| WO | WO 84/02423 | 6/1984 |
| WO | WO 98/02088 | 1/1998 |
| WO | WO 02/089906 | 11/2002 |
| WO | WO 2011/106730 | 9/2011 |
| WO | WO 2011/154210 | 12/2011 |
| WO | WO 2013/049467 | 4/2013 |

OTHER PUBLICATIONS

Eurostar Engineering Plastics, "Starglas BX06088", last updated Jan. 7, 2010, available online at https://www.eurostar-ep.com/wp-content/uploads/pdfs/4827/TDS_Starglas_BX06088.pdf (Year: 2010).*
PCT International Search Report for PCT/US2016/063956 dated Mar. 6, 2017.
"Conductive polymer" from Wikipedia, the free encyclopedia; Dec. 11, 2015; 6 pgs; available at https//web.archive org/web/20151211045601/ https://en.wikipediaorg/wiki/Conductive_polymer (XP055347878).
"Poly(p-phenylene sulfide)" from Wikipedia, the free encyclopedia; May 8, 2015; available at https://web.archive.org/web/20150508022926/http://en.wikipedia.org/wiki/Polyphenylene_sulfide (XP055347876).
"Ryton—Polyphenyl Sulfide, Polymer Plastics Company, LC, Carson City, Nevada;" Sep. 16, 2015; available at https://web.archive.org/web/20150916115247/http://www.polymerplastics.com/performance_ryton.shtml (XP055347872).
International Search Report for PCT/US2015/064920 dated Mar. 16, 2017.
International Search Report for PCT/US2015/063948 dated Mar. 17, 2017.

* cited by examiner

ONE-PIECE SENSOR FOR A BIOELECTRODE AND PROCESSES FOR PRODUCTION

CROSS REFERENCE TO RELATED APPLICATIONS

This application is a national stage filing under 35 U.S.C. 371 of International Application No. PCT/US2016/063956, filed Nov. 29, 2016, which claims the benefit of U.S. Provisional Application No. 62/270,649, filed Dec. 22, 2015. The disclosures of both applications are incorporated by reference in their entirety herein.

This application relates to medical devices, in particular to sensors for medical electrodes and methods of producing sensors and medical electrodes.

BACKGROUND

Electrocardiogram (ECG) electrodes usually rely on silver coated eyelets for operation. The eyelet is usually physically mated through a tape or backing with a metallic or plastic stud or snap. This interaction holds the eyelet onto the adhesive portion of the web and ensures a good moisture seal through the electrode backing. Eyelets are usually fabricated by injection molding an ABS resin to produce a discrete part and coating the entire part with silver. Using parts produced in this manner requires handling and assembly of discrete parts during electrode fabrication. The process of snapping the eyelet and stud together can be problematic in the fabrication process and also be a limiting step on productivity rates. There are commercial examples of electrodes with a one-piece sensor, but there is usually an additional feature for holding the eyelet in place, such as a retaining washer, reinforcing strip or the like which does not remove this complexity issue.

For example, Con-Med makes a resting electrode (Snap-Trace™ II) that utilizes a one piece sensor, but it is a discrete part held attached by the backing skin adhesive, and this sensor is completely coated with silver-silver chloride. Another example is the Con-Med DYNA/TRACE™ 1500 ECG Electrode that utilizes a one-piece sensor, which is a discrete part attached by a backing skin adhesive on one side and by retaining washers on the post side.

SUMMARY

There remains a need for a simpler, more efficient method of producing one-piece sensors for ECG electrodes and one-piece sensors produced thereby that do not require additional retaining elements to retain the sensor on the electrode.

There is provided a process for producing a sensor for a biomedical electrode, comprising: injection molding an electrically conductive resin through a film of a backing material to form the sensor directly in the backing material, the sensor comprising a contact face disposed on a first side of the film and a post protruding from a second side of the film opposite the first side; and, coating the contact face with a non-polarizable conductive material.

There is further provided a process for producing a biomedical electrode, comprising: forming a sensor directly in a backing material by injection molding an electrically conductive resin through a film of the backing material, the sensor comprising a contact face disposed on a first side of the film and a post protruding from a second side of the film opposite the first side; coating the contact face with a non-polarizable conductive material; applying an electrolyte over the non-polarizable conductive material coated on the contact face; and, applying a liner over the electrolyte.

There is further provided a biomedical electrode comprising a sensor secured in a film of a backing material with a contact face of the sensor disposed on a first side of the film and a post of the sensor protruding from a second side of the film opposite the first side, the sensor formed by injection molding an electrically conductive resin through the film.

There is further provided a biomedical electrode produced by the above described process.

There is further provided a process for producing a web of electrically conductive structures, comprising: injection molding an electrically conductive resin through a film of a backing material to form the structures directly in the backing material, the structures comprising a flange disposed on a first side of the film and a post protruding from a second side of the film opposite the first side.

There is further provided a web of electrically conductive structures comprising a plurality of electrically conductive structures comprising an electrically conductive resin injected molded through a film of backing material, each electrically conductive structure comprising a flange and a post extending away from the flange, the flange disposed on a first side of the film and the post protruding from a second side of the film opposite the first side.

The processes permit production of bioelectrodes in a continuous fashion without the need for studs or other retaining features to retain sensors on a film of the backing material. The processes may be tailored to meet varying conductivity and size requirements, dependent on the required electrode performance. Molding the sensor directly in a film of the backing material may lead to one or more of: eliminating the need for a retaining snap or stud, which will additionally reduce the chance of corrosion from dissimilar metals; improving dry out performance of electrodes; reducing amount of non-polarizable conductive material (e.g. silver-containing material) to only what is functionally required; simplifying and reducing the total number of assembly steps; and reducing dimensional high tolerance requirements for the sensor's post because precise dimensions for mating the post to a stud are not required to ensure electrical continuity and interference fit.

The processes potentially enable easier electrode assembly, while reducing costs by removing the need for a stud and the need to electroplate the entire sensor with non-polarizable conductive material (e.g. a silver-containing material). By forming the sensor directly through the web, molten resin may thermally bond with the film of backing material removing the need for a film-retaining feature. A film-retaining feature integrally molded on the sensor upon injection molding may be utilized instead of or in addition to thermal bonding. A film of backing material with an adhesive layer may be utilized instead of or in addition to thermal bonding and/or an integrally molded film-retaining feature. By molding the sensors as opposed to feeding discrete sensors, an array of sensors on the web may be positioned in any configuration, providing flexibility and potentially greater output for a continuous production process.

DETAILED DESCRIPTION

Webs of electrically conductive structures produced in accordance with the processes comprise structures having a flange and a post. In one embodiment, these structures may be suitable for sensors for biomedical electrodes. Thus, a fabrication method for producing 3-dimensional sensors for use in biomedical electrodes, preferably electrocardiogram (ECG) electrodes, is also provided. In the processes, structures (e.g. sensors) are injection molded and coated with non-polarizable conductive material directly on a film of backing material. This is in contrast with methods of snapping a discrete silver-coated part with a mating retaining feature through a film. The film with the sensor may be then further used to complete electrode assembly.

The processes comprise injection molding an electrically conductive resin through a film of a backing material to form the structure (e.g. sensor) directly in the backing material. Methods of injection molding a molded article on to a web are disclosed in U.S. Pat. No. 8,637,136 issued Jan. 28, 2014 and U.S. Patent Application Publication No. 2010/0159197 published Jun. 24, 2010, the contents of both of which are herein incorporated by reference. Such methods may be adapted in the present invention to permit injection molding of a structure (e.g. sensor) through a web of backing material by providing a mold that has features in one mold half to create the flange and features in another mold half to create the post and any integrally formed film-retaining features that may be present on the structure (e.g. sensor). Injecting the conductive resin through the mold gate can then fill the two halves by forcing molten resin through the film between the mold halves. A partially-continuous process may be accomplished by opening the mold halves after resin injection and advancing a continuous film of the backing material, closing the mold halves and injecting more resin to form another structure (e.g. sensor). The first structure (e.g. sensor) will have advanced away from the mold and may be coated with the non-polarizable conductive material at a next station while the second structure (e.g.) sensor is being formed at the injection molding station. Further advancement of the continuous film would bring successive structures (e.g. sensors) through successive stations, for example stations for applying the electrolyte over the non-polarizable conductive material, for applying a liner over the electrolyte and/or for packaging the electrodes. The structures (e.g. sensors) may be separated from the continuous film after any station in the process, for example separated by cutting (e.g. die cutting, laser cutting and the like). The entire process for forming the electrode may be completed before separation of individual electrodes from the web. However, separation may occur before or after any one of applying the non-polarizable conductive material, applying the electrolyte, applying the liner or packaging. Additionally, the electrodes may not be separated from the web and instead wound up as a roll or collected as a web for use in another process. It should be understood that the entire process need not be continuous, but may be conducted with injection molded structures (e.g. sensors) in discrete web sections; however, a partially or fully continuous process is used in some embodiments. Not having discrete parts in the electrode assembly process removes much of the complexity and the limitations they cause on production speed, line width, etc.

Further, a plurality of sensors may be formed across and along a single film providing sensors formed in a plurality of rows or other arrangements across the width and along the length of the film. Such arrangements permit a multi-lane (e.g. 2, 3, 4, 5 or more lanes) continuous process, in addition to permitting varying pitch spacing, which may dramatically increase electrode production in a given time frame. Thus, webs produced in the process may comprise a plurality of rows of structures across a width of the film, for example 2, 3, 4, 5 or more rows. The web may comprise at least 5 rows of structures, for example at least 6 rows, at least 8 rows or at least 10 rows.

Webs of electrically conductive structures (e.g. sensors) produced in accordance with the processes comprise structures having a flange and a post. The flange may comprise a contact face that comprises an imperfection at a location where a mold gate of a mold was situated for injection molding of the structure. The electrically conductive resin of the structure may comprise conductive fibers, and the fibers may be oriented generally perpendicular to the contact face at the imperfection. Further, a portion of each post proximal the flange may be covered by the film. Hereinafter, the term "sensor" is used, although the description in at least some instances may be applicable to the more generic term "structure".

The production process may be tailored to produce sensors that are visually different or visually the same as existing sensors or studs. For example, the sensor may be molded onto a laminate of tape on top of foam with a well to create an electrode that would look the same as some of the current 3M Company electrodes. Web injection molding also permits entirely new electrode designs. Specific design requirements may be met by providing a suitable mold to meet sensor requirements, and suitable changes in other process steps to produce a final electrode design tailored for a specific application. Further, a suitable mold may be designed to form the web suitably during the injection molding step to give the web a recessed feature, which can be used as a storage well for an electrolyte gel.

The conductive resin may comprise any injection moldable resin suitable for use in electrodes. The resin may comprise a thermoplastic resin, an elastomeric resin, a thermoset resin, copolymers thereof or any blend or mixture thereof. Thermoplastic resins, elastomeric resins, copolymers thereof or any blend or mixture thereof are used in some embodiments. Some particular examples include polyolefin (e.g. polypropylene, such as low density polypropylene), polyacrylate, polyethylene terephthalate (PET), acrylonitrile-butadiene-styrene (ABS), poly(dimethylsiloxane) (PDMS) and ethylene propylene diene monomer (EPDM) resin. The resin may comprise usual additives in the polymer industry. For use as in electrodes, it is desirable to confer electrical conductivity on the bulk of the resin by using electrically conductive polymers and/or by dispersing one or more electrically conductive fillers in a resin matrix. Some examples of electrically conductive polymers include doped polyolefins, polythiophenes, polypyrroles and the like. Some examples of electrically conductive fillers include metals (e.g. nickel, iron, and the like), conductive carbonaceous material (e.g. graphite, polyacrylonitrile (PAN)), carbon black, nano graphite platelets, carbon fibers or particles of the inherently conductive polymers listed above). Conductive carbonaceous material is used in some embodiments. The electrically conductive filler may be in the form of substantially spherical, flakes, fibers or any mixture thereof. Fibers are used in some embodiments. Conductive carbonaceous filler may be dispersed in the resin matrix in any suitable amount that provides a desired electrical performance while maintaining processability of the conductive resin. For many applications, an amount of conductive filler in a range of about 20-60 wt %, based on total weight of the conductive resin, may be suitable. In some embodiments, the amount of conductive filler may be controlled in a range of about 25-50 wt % or about 30-40 wt %.

The backing material may be any suitably handleable material used to provide a backing film in a biomedical electrode. The backing film is on a side of the sensor away from the layer of non-polarizable conductive material coated on the contact face. The backing film may provide support for the sensor and/or a convenient place to handle the electrode without damaging the sensor and/or any conductive gel or adhesive in the electrode. The backing material in some embodiments comprises a polymeric resin, such as a thermoplastic or elastomeric resin. Some examples include polyethylene terephthalate, polyolefins (e.g. polypropylene, etc.), polystyrene, acrylonitrile butadiene styrene (ABS), ethylene-vinyl acetate (EVA), silicone rubbers. Additionally, non-polymeric backings may be used, for example paper-like products or cloth-like films and non-woven films. A plurality of layers of backing material may be utilized, where each layer may comprise the same or different material as other layers. Layers may be added before or after injection molding the sensor through the backing film. In a finished electrode, one of the layers of the backing film may be a solid foam, or the backing film may be adhered over an open cavity (gel well) of a solid foam web. A solid foam web is preferably not used in the injection molding step due to the thickness of the foam web. However, the solid foam web, whether part of the backing film or adhered later to the backing film, is useful for conforming and adhering the electrode to the subject's skin. The backing film may also comprise an adhesive layer to enhance adhesion of the sensor to the film and adhesion of the backing layer to other electrode components during further processing or to the patient's skin.

The process may employ any one or more of a variety of non-polarizable conductive materials including inks, coated particles, pure materials and the like. The non-polarizable conductive material in some embodiments comprises a non-polarizable conductive metal-containing material. The metal in the metal-containing material in some embodiments comprises silver or iron. In a one embodiment, the non-polarizable conductive material includes silver inks, silver-coated particles, silver metal and the like. The non-polarizable conductive material may be provided in different forms, for example as a liquid, a pre-formed film and the like. The process is especially suited to applying an ink. Inks may be applied using any one of a number of techniques including, for example, screen printing, inkjet printing, gravure printing, flexographic printing, offset printing, transfer, in mold decoration, etc. However, other methods of applying a non-polarizable conductive material may be utilized, for example sputtering, thermal evaporation/deposition, electroplating, electro-less plating, etc. Inks comprise particles (e.g. nanoparticles, flakes) dispersed in a solvent usually with a binder. The solvent may comprise an aqueous solvent or an organic solvent (e.g. benzene, toluene, ethylbenzene, xylenes, chlorobenzene, benzyl ether, anisole, benzonitrile, pyridine, ethylbenzene, propylbenzene, cumene, isobutylbenzene, p-cymene, indane, tetralin, trimethylbenzenes (e.g. mesitylene), durene, p-cumene, indane, tetralin or any mixture thereof) and the binder generally comprises a polymeric material (e.g. ethyl cellulose, hydroxypropyl cellulose, hydroxymethyl cellulose, hydroxyethyl cellulose, polypyrrolidone, polyvinylpyrrolidones, epoxies, phenolic resins, acrylics, urethanes, silicones, styrene allyl alcohols, polyalkylene carbonates, polyvinyl acetals, polyesters, polyurethanes, polyolefins, fluoroplastics, fluoroelastomers, thermoplastic elastomers or any mixture thereof).

Some types of electrodes require the non-polarizable conductive material component to be partially converted to an ionic state in order to function, for example in order to interact with different electrolyte gels. Where the non-polarizable conductive material comprises a metal-containing material, elemental metal in the non-polarizable metal-containing material may be partially oxidized. The non-polarizable metal-containing material would then comprise metal in the 0 oxidation state along with one or more cations of the metal. In the case of silver, the silver may be pre-chlorinated to produce some $Ag^+$ ions in the silver-containing material. In such applications, the coating of silver-containing material may be partially pre-chlorinated to provide a mixture of silver (Ag) and silver chloride (AgCl) in the layer. Chlorination of the silver may be accomplished by any suitable method, for example by reacting the silver with a chlorinating agent. Chlorinating agents include, for example, chlorite ($ClO_2^-$). The silver may be chlorinated to provide a desired ratio of silver to silver chloride provided there is sufficient silver remaining for the desired function and performance. Alternatively or additionally, a commercially available silver/silver chloride ink can be coated onto the smooth portion of the web to remove the need for chlorinating the printed silver, for example as described in U.S. Pat. No. 4,377,170 published Mar. 22, 1983, the contents of which is herein incorporated by reference. In the case of iron, the iron may be partially oxidized to iron (II) and a counterion anion (e.g. sulfate) used to balance the charge. A mixture of iron (Fe) and ferrous ions (e.g. in the form of ferrous sulfate ($FeSO_4$)) would be present in the layer.

Once coated on the contact face of the sensor, an ink may be dried and sintered using known regimes to adhere the ink to the contact face of the sensor. Drying may be performed at ambient temperature or elevated temperature and sintering is typically performed at elevated temperature for a prescribed period of time in accordance with the ink manufacturer's specification. Ovens are typically used for sintering, and drying in many cases, and may be incorporated into a production line.

The sensors produced by injection molding the conductive resin through the film of backing material may be processed into electrodes, especially electrodes for electrocardiography (ECG), together with other electrode components. The electrode may be of any style in which a surface coated with non-polarizable conductive material is applicable, for example monitoring ECG electrodes, resting (tab) ECG electrodes, EMG electrodes, stimulation electrodes and the like. Electrodes comprise the sensor in the film of backing material and one or more other components to complete electrode construction. The sensor comprises a contact face through which electrical signals are received from the subject's skin. To enhance electrical contact between the subject's skin and the contact face of the sensor, the electrode may further comprise a conductive gel or adhesive (an electrolyte) that acts as a conformable conductive interface between the sensor and the subject's skin. In the case of a conductive adhesive, the adhesive also helps secure the electrode to the skin. Where a gel or adhesive is used, the electrode may comprise a removable cover or liner to protect and contain the gel or adhesive before use. The cover or liner may be removed to expose the gel or adhesive just before use. The sensor comprises one or more posts that act as lead terminals to which electrical leads may be attached, the electrical leads carrying electrical signal back to an output device. Electrical signals from the subject's skin are conducted through the face coated with non-polarizable conductive material (or the conductive gel or adhesive and then the face coated with non-polarizable conductive material) though the bulk of the sensor, which comprises electrically conductive resin, through the post into the leads and thence to the output device. Although not required, in some cases, one or more electrically conductive studs (e.g. made of brass, stainless steel or the like) may be used to cover the post. However, obviating the necessity to use studs is one of the advantages of the present process. The electrode arrangement is not particularly limited and the sensor may be used in any of a wide variety of electrode arrangements.

Figure 1:
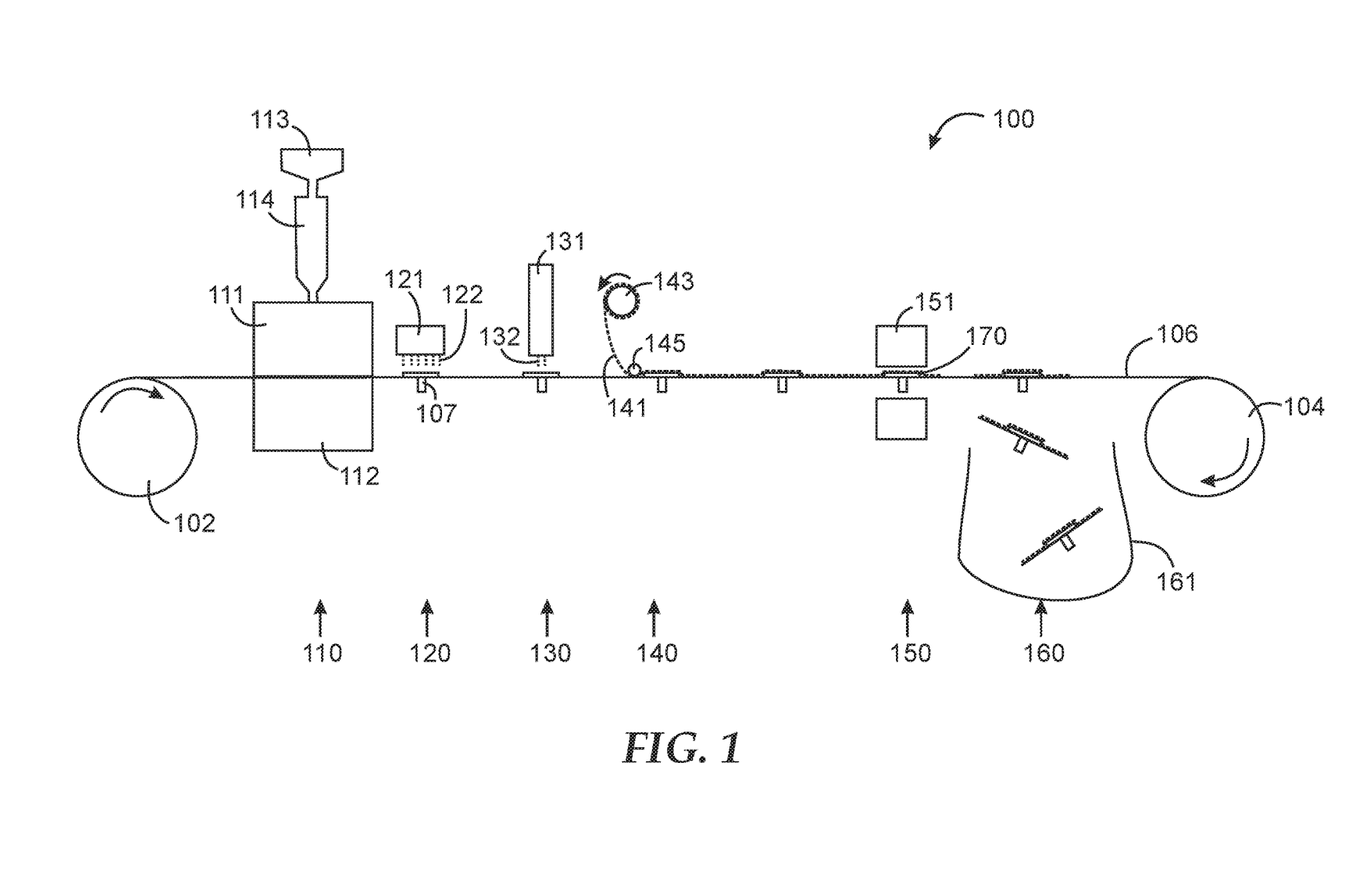
FIG. 1 depicts a schematic diagram illustrating a continuous process in accordance with the present invention for production of one-piece bioelectrodes.

FIG. 1 illustrates one embodiment of a continuous production process for one-piece electrodes. A production line 100 comprises a continuous film feed system comprising a film feed roll 102 and a driven film uptake roll 104 between which a film 106 of backing material is advanced through the production line 100. The film 106 is first fed through an injection molding station 110 between mold halves 111, 112. Upper mold half 111 is designed with features to produce flanges of sensors 107 (only one labeled), while lower mold half 112 is designed with features to produce a post of the sensors. Conductive resin stored in a hopper 113 is fed into an injector 114 where the resin is melted and then injected into the mold. In this embodiment, the conductive resin is injected into the upper mold half 111 and allowed to flow through the film 106 into the lower mold half 112 to form the entirety of the sensors through and in the film 106. Temperature of the resin during injection molding may affect the strength of the thermal bond between the conductive resin of the sensors 107 and the backing material of the film 106. The resin is preferably injected at a sufficient temperature such that molten resin in the mold can thermally bond with the backing material. For example, for polypropylene backing material, resin temperature during molding is in a range of about a 150-315° C., or about 230-275° C. in some embodiments.

Once injection is complete, the sensors 107 are allowed to solidify, the mold halves 111, 112 are separated and movement of the continuous film 106 advances the sensors 107 to a printing station 120. The printing station 120 comprises an ink printer 121, which is used to coat the contact face of the sensors 107 with ink 122, for example by screen printing, ink jet printing or any other suitable printing method. The printing station 120 may also comprise an oven for drying and sintering the ink 122 on the contact face of the sensor 107, or the ink may be air dried and sintered in an oven downstream in the process. The sensors 107 coated with non-polarizable conductive material are then advanced to an electrolyte application station 130 where the coated contact faces of the sensors 107 are further coated with a conductive gel or adhesive 132 using an electrolyte applicator 131. In embodiments where a gel is used, to facilitate retention of the gel 132, the film 106 may be a foam material having wells formed therein within which the sensors 107 are injection molded so that the wells are able to retain the gel over the contact faces of the sensors 107. Alternatively, when using a thin web/tape as the backing film through which to inject the sensors, a piece of open cell absorbing foam can be secured on top of the sensor to contain the gel. Various suitable kinds of conductive gels and adhesives are known in the art. The gel- or adhesive-coated sensor is then advanced to a liner application station 140 where a liner 141 (shown in dashed lines) is applied over top of the coated contact faces of the sensors 107 to protect the conductive gel or adhesive during handling and to provide a seal for moisture retention of the gel. The liner 141 may be applied by any suitable method. Depicted is a roll application method in which the liner 141 is continuously fed from a feed roll 143 and held in contact with the film 106 by a press roll 145. The liner 141 adheres to the film 106 to cover the coated sensors 107 to produce electrodes 170 formed in the continuous film 106. Some liner materials are polyethylene terephthalate (PET), high impact polystyrene and polyethylene coated paper.

In this embodiment, up to the liner application station 140, all of the sensors 107 are contained in a continuous web. While separation of the sensors 107 from the web may be done at any stage of the process, this embodiment illustrates separation of the formed electrodes 170 after the liner 141 is applied, however separation may be performed, if desired, before the printing station, after the printing station but before the electrolyte application station or after the electrolyte application station but before the liner application station. Thus, separation may be accomplished at any place in the process after molding of the sensors. Separation is performed at a separation station 150 and may be performed by any suitable method, for example die cutting with a die cutter 151. The electrodes containing the one-piece sensor may be separated individually, or separated as 'cards' or clusters of electrodes on one piece of liner. The separated electrodes, individually or as cards of electrodes, 170 are advanced to a packaging station 160 where the electrodes 170 may be packaged and/or collected, for example placed in moisture proof bags 161. Separating the electrodes 170 may be performed in a manner whereby the continuous film 106 retains sufficient integrity that collection of the film 106 on the uptake roller 104 can still be done to advance the length of the film 106 through the process.

While separation of the sensors from the web is an embodiment of the process, the process may also encompass not separating the sensors and using the web with a plurality of the sensors formed therein in another assembly process. Any time after the sensors are injected molded through the film, the web may be collected and transferred to the other assembly process. The web may be collected by any suitable method, for example by rolling up the web as the web proceeds along the production line to form a roll of the web with the sensors molded therein. Collecting the web may be performed before the printing station, after the printing station but before the electrolyte application station, after the electrolyte application station but before the liner application station, or after the liner application station but before the separation station. Thus, the web with the sensors molded therein may be collected for future processing at any place in the process after molding of the sensors and prior to separation.

Figure 2A:
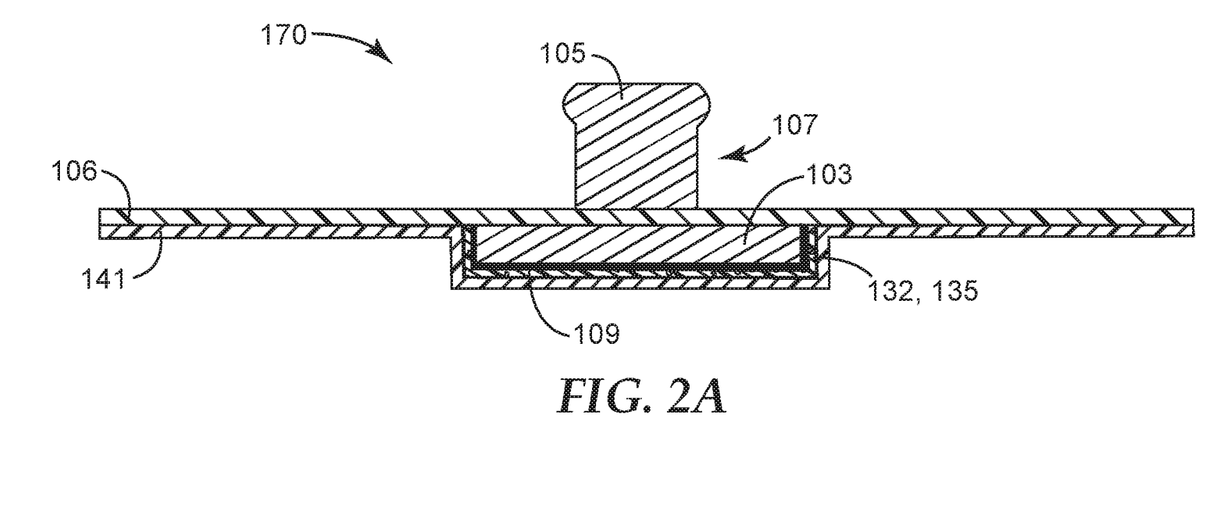
FIG. 2A depicts a side cross-sectional view of a fully assembled electrode produced by the process of FIG. 1.

FIG. 2A depicts a side cross-sectional view of a fully assembled electrode 170 produced by the process of FIG. 1. The electrode 170 comprises the sensor 107 molded through and anchored in the backing film 106. The sensor 107 comprises a flange 103 having a contact face coated with a layer 109 of non-polarizable conductive material (e.g. silver-containing material), and the contact face is the primary surface of the sensor 107 through which electrical impulses from a subject will be received during use of the electrode 170. The sensor 107 further comprises a post 105 extending through the film 106 to extend away from the film 106 on an opposite side of the film 106 from the flange 103. The flange 103 is embedded in an open cell absorbing foam layer 135 containing the conductive gel 132 so that the conductive gel 132 is in contact with the layer 109 of non-polarizable conductive material. The liner 141 covers the film 106 and the foam layer 135 to protect the foam layer 135 and the conductive gel 132 therein.

Figure 2B:
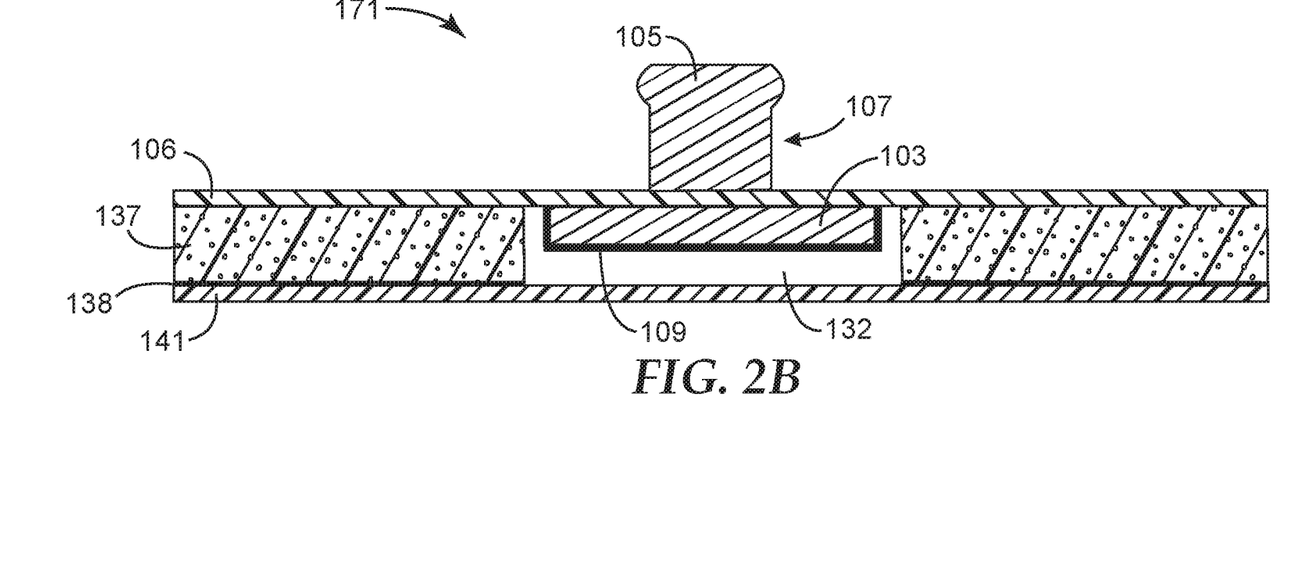
FIG. 2B depicts a side cross-sectional view of another embodiment of a fully assembled electrode producible by the process of FIG. 1.

FIG. 2B depicts a side cross-sectional view of another embodiment of a fully assembled electrode 171 producible by the process of FIG. 1. The electrode 171 comprises the sensor 107 molded through and anchored in the backing film 106. The sensor 107 comprises a flange 103 having a contact face coated with a layer 109 of non-polarizable conductive material (e.g. silver-containing material), and the contact face is the primary surface of the sensor 107 through which electrical impulses from a subject will be received during use of the electrode 171. The sensor 107 further comprises a post 105 extending through the film 106 to extend away from the film 106 on an opposite side of the film 106 from the flange 103. In contact with the layer 109 of silver-containing material is a conductive gel 132 contained within the electrode 171 at the flange 103 in a well in a closed cell foam layer 137 secured to the backing 106. The liner 141 covers the foam layer 137 and the well in the foam layer 137 to protect and contain the conductive gel 132 and to protect a layer of skin adhesive 138 on foam layer 137.

Figure 3:
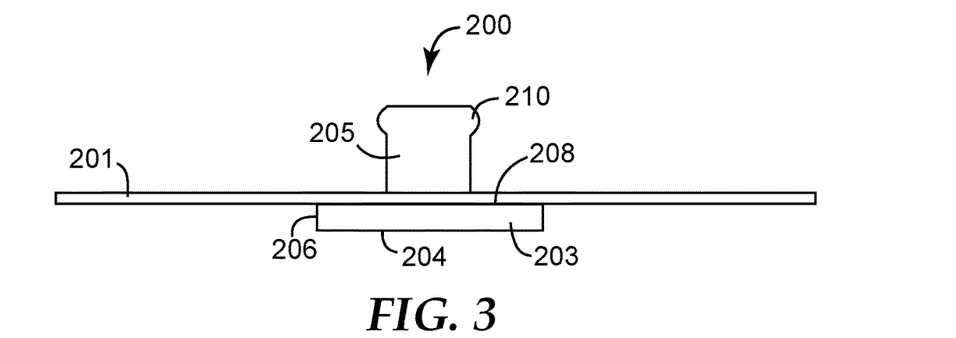
FIG. 3 depicts a side view of a sensor injection molded through a thermoplastic polymer film and secured to the film by a thermal bond between the sensor and the film.
Figure 4:
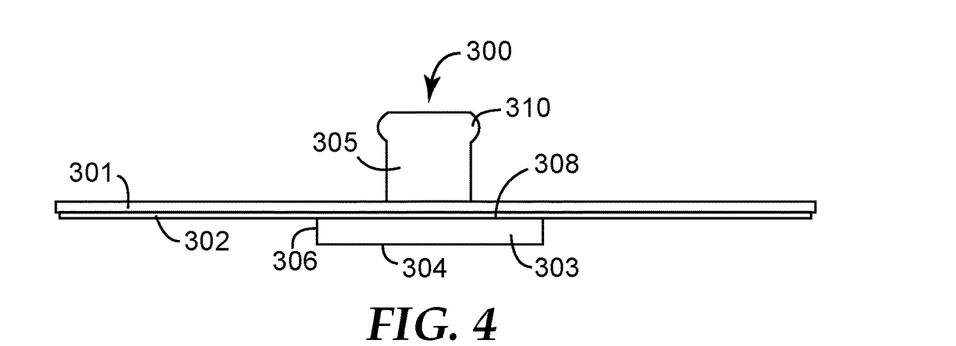
FIG. 4 depicts a side view of a sensor injection molded through a thermoplastic polymer film and secured to the film by an adhesive bond between the sensor and the film.
Figure 5:
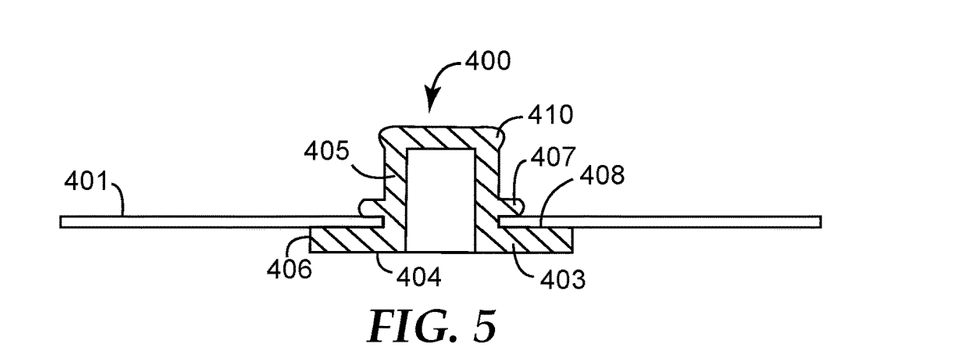
FIG. 5 depicts a side cross-sectional view of a sensor injection molded through a thermoplastic polymer film and secured to the film by molded parts of the sensor that cooperate to pinch the film between the molded parts.

Depending on the application of the electrode and the types of materials utilized for the backing material, injection molding the conductive resin through the backing material may be tailored to provide different ways in which the sensor is secured in the backing film. Features may be included in the mold halves to provide the specific design specifications for each sensor depending on the backing material used. FIG. 3, FIG. 4 and FIG. 5 illustrate three embodiments.

FIG. 3 depicts a first embodiment of a sensor 200 injection molded through a backing film 201. The sensor 200 comprises a flange 203 having a contact face 204 and a circumferential or perimetrical edge 206. The flange may be of any suitable shape (e.g. circular, square, etc.) and may be solid or contain one or more vacancies to reduce material consumption, provide some flexibility, contain other kinds of material or for other purposes. Vacancies may be, for example, an aperture in the flange 203. The flange 203 is disposed on one side of the film 201 with the contact face 204 facing away from the film 201. The contact face 204 will be coated with non-polarizable conductive material (e.g. silver-containing material) and will be the primary surface of the sensor 200 through which electrical impulses from a patient will be received during use of the electrode. The sensor 200 further comprises a post 205 extending through the film 201 to extend away from the film 201 on an opposite side of the film 201 from the flange 203. A distal end of the post 205 comprises a bulb or enlarged portion 210 to which electrical leads may be attached. Sensor 200 is secured to the film 201 by a thermal bond created when molten conductive resin of the sensor 200 interacts with the backing material of the film 201 during injection molding. An interface between the surface of the film 201 and a film facing surface 208 of the flange 203 provides the majority of the bonded area.

FIG. 4 depicts a second embodiment of a sensor 300 injection molded through a backing film 301. The sensor 300 comprises similar features to the sensor 200 depicted in FIG. 3, including an annular flange 303 having a contact face 304, a circumferential edge 306 and a film facing surface 308, and a post 305 comprising a bulb or enlarged portion 310 at a distal end of the post 305. Unlike the sensor 200 depicted in FIG. 3, the sensor 300 is secured to the backing film 301 by the thermal bond between the conductive resin and an adhesive layer 302 between the film 301 and the film facing surface 308 of the flange 303 of the sensor 300. The adhesive layer 302 will also serve to secure a liner over the electrolyte coated flange during production of an electrode and secure the electrode to a subject's skin.

FIG. 5 depicts a third embodiment of a sensor 400 injection molded through a backing film 401. The sensor 400 comprises similar features to the sensor 200 depicted in FIG. 3, including an annular flange 403 having a contact face 404, a circumferential edge 406 and a film facing surface 408, and a post 405 comprising a bulb or enlarged portion 410 at a distal end of the post 405. Unlike the sensor 200 depicted in FIG. 3, the sensor 400 is secured to the backing film 401 by an integrally formed film-retaining feature 407 molded into the sensor 400 during injection molding. The film-retaining feature 407 may comprise an annular ring molded around the post 405 and spaced apart from the film facing surface 408 of the flange 403 by an amount about equal to or somewhat less than the thickness of the film 401. Other variations on the film-retaining feature may be contemplated. Because the film-retaining feature 407 is an integral part of the sensor 400 fabricated during molding of the sensor 400, separate parts and extra process steps are not required.

Figure 6:
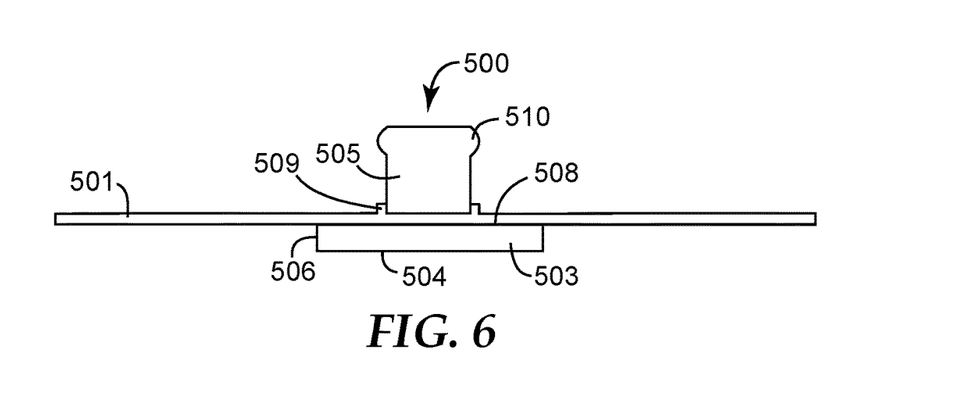
FIG. 6 depicts a side view of a sensor injection molded through a thermoplastic polymer film and secured to the film by an adhesive bond between the sensor and the film, with the film adhering to a portion of a post of the sensor part way up the post.

FIG. 6 depicts another embodiment of a sensor 500 injection molded through a backing film 501. The sensor 500 comprises a flange 503 having a contact face 504 and a circumferential or perimetrical edge 506. The flange 503 is disposed on one side of the film 501 with the contact face 504 facing away from the film 501. The contact face 504 will be coated with non-polarizable conductive material (e.g. silver-containing material) and will be the primary surface of the sensor 500 through which electrical impulses from a patient will be received during use of the electrode. The sensor 500 further comprises a post 505 extending through the film 501 to extend away from the film 501 on an opposite side of the film 501 from the flange 503. A distal end of the post 505 comprises a bulb or enlarged portion 510 to which electrical leads may be attached. Sensor 500 is secured to the film 501 by a thermal bond created when molten conductive resin of the sensor 500 interacts with the backing material of the film 501 during injection molding. An interface between the surface of the film 501 and a film facing surface 508 of the flange 503 provides the majority of the bonded area. However, due to injection molding conditions, a raised portion 509 of the film 501 is adhered to and surrounds a portion of the post 505 proximal the film facing surface 508 of the flange 503. The raised portion 509 forms a circumferential or perimetrical ring around a base of the post 505.

Figure 7:
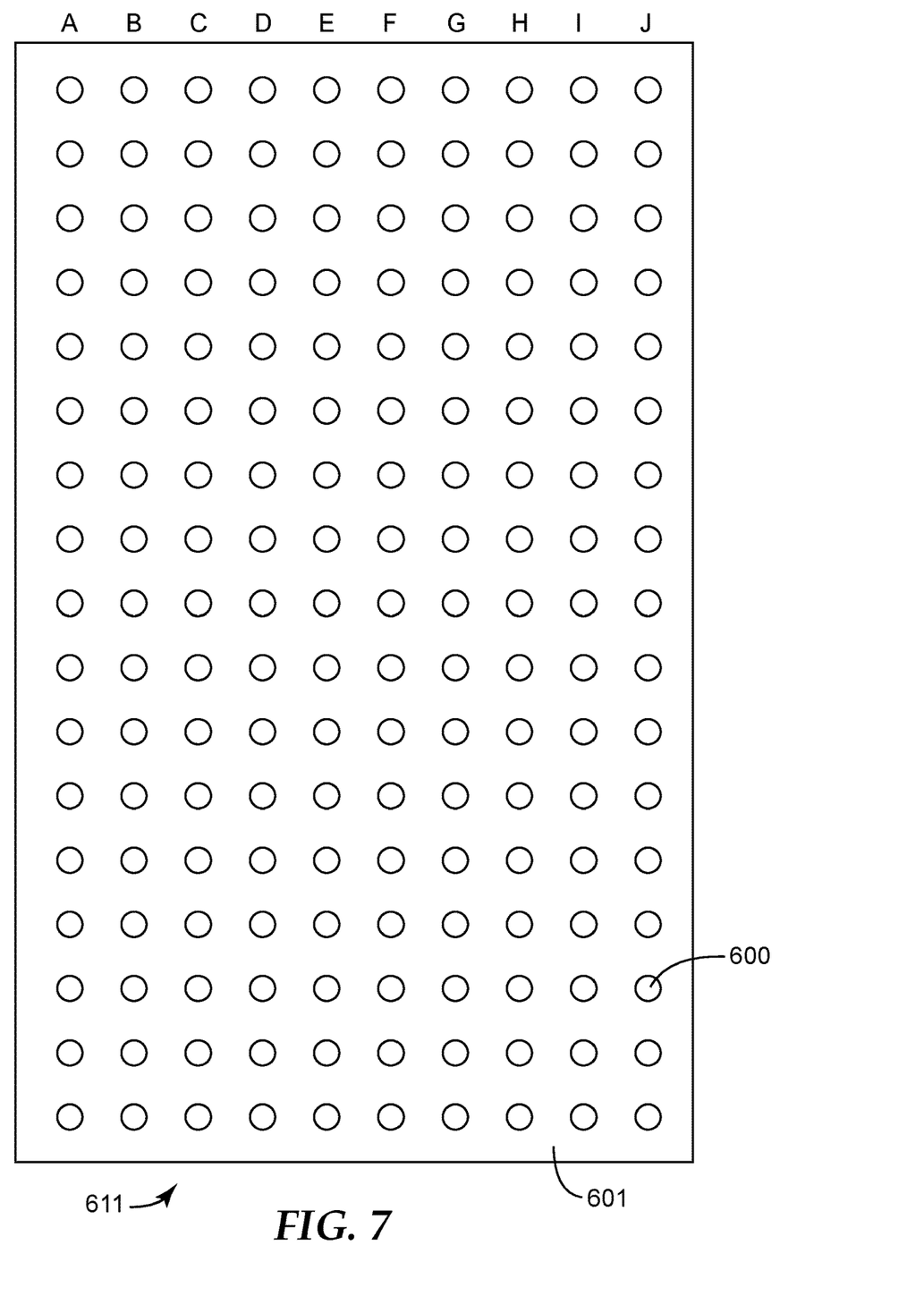
FIG. 7 depicts a plan view of a web of electrically conductive structures injection molded through a film, the web comprising an array of 10 rows of structures across a width of the film.

FIG. 7 depicts a web 611 of electrically conductive structures 600 (only one labeled) injection molded through a film 601, the web 611 comprising an array of 10 rows A-J of structures 600 across a width of the film 601. Each row of structures 600 is depicted having 17 structures 600 along the length of the row; however, both the number of rows and the length of the web 611 are not particularly limited except by production plant practicalities. The web 611 may be further processed to produce sensors from the structures 600, or the web 611 may be rolled up and stored or used in a different process.

EXAMPLES

Materials and Preparation of Electrically Conductive Resin

Conductive resin for sensor fabrication was compounded with established melt processing techniques known in the art. The compounding can be conducted in batch form with the resin collected and ground to fine particles, or in a continuous manner to form pellets. A matrix polymer with good affinity for carbon fibers was important to create easy percolation at significant carbon fiber loading. Polypropylene was chosen as the composite matrix due to ease of manufacturing and low cost. After trials, polypropylene grade 5476X from Total petrochemicals it was chosen for dispersing the carbon fibers and enabling easy injection molding.

Carbon fibers from TOHO TENAX (PCS082501 grade) were used as is. The carbon fibers had been surface modified by the supplier with proprietary chemicals to enable easy dispersion and bonding with the polypropylene resin. Carbon fiber was added at various weight percentages into the polypropylene matrix and electrical conductivity was measured. It was found that 30 wt % carbon fiber was sufficient for lower-end sensor parts, while upwards of 40 wt % could produce sensors that matched or exceeded current commercial parts.

Other commercially available conductive resins, such as carbon fiber loaded ABS resin RTP 687 grade, or carbon fiber loaded polypropylene ESD C 180 grade, both from RTP Company (Winona, Minn.), are other specific examples of conductive resins.

Example 1: Injection Molding of a Sensor Through a Film

A small lab scale mold was fabricated having a design to produce one-piece sensors having a shape such that it would connect to the current industry standard lead wires. A few changes from the currently used shape were implemented to produce a sensor 400 as depicted in FIG. 5. First, the bulb 410 (i.e. the larger diameter section at the end of the post 405) was created using appropriately designed injectors (purchased from Tulip™ Medical Products). This enabled molding of the entire sensor 400 in one step, with the parting line perpendicular to the post axis. This change facilitates injection molding through the film 401, as opposed to the current injection molded sensors which have a parting line parallel to the post axis and does not mold the sensors through a film. An additional change was the molding of a film-retaining feature 407 directly into the sensor 400. The film-retaining feature 407 permits pinching of the film 401 between the film-retaining feature 407 and the flange 403 to help retain the sensor 400 on the film 401 if there was no thermal bond between the sensor 400 and the film 401. Also, the gate location was changed because molding through the film 401 requires resin to flow in a particular pattern, which is not required in normal molding. Post-processing steps that are currently used for the discrete parts would be difficult to implement. One such post-process step is tumbling the sensors, which removes the flash on the parting line and to visually remove the gate location. Since the sensor 400 will be coated with a silver-containing material on the contact face 404, the gate location was chosen to be on the contact face 404 at or near the edge 406 of the contact face 404, where the gate location may be easily hidden by the application of the silver-containing material. This gate location also presented a unique opportunity for enhanced conductivity. Since the conductive resin is entering the mold at the gate location, the orientation of the carbon fibers is generally perpendicular to the contact face 404 at this location. Thus, edges of carbon fiber are generally exposed and once coated with silver-containing material, present a very low electrical resistance path into the bulk of the sensor 400.

Various backing materials were tested as film inserts for compatibility with the carbon fiber filled polypropylene molded sensors. While all worked in the sense that a sensor was able to be molded through and onto the film that met dimensional standards and conductivity tests, some backing materials were more effective, e.g. polypropylene (PP) and polyethylene terephthalate (PET). Polypropylene sensors inserted through the film resulted in very good thermal bonding of the sensor to the film, but the polypropylene film became too soft when in contact with the melt, which resulted in the web bowing out and residing on top of the film-retaining feature. However, with the good thermal anchorage on the back of the flange, the film-retaining feature would not be needed for a polypropylene film and a sensor may be injection molded through a polypropylene film as illustrated in FIG. 3. For a film of PET, the molded sensor did not thermally bond as well to PET film, but the film-retaining feature worked very well in anchoring the sensor to the film. However, a further processing step to reduce water vapor transmission through the connection between the PET film and the sensor may be useful to optimize performance. For example, application of a sealant, use of an adhesive on the film surface, or use a PET film having a PP layer on side 408, would help reduce such water vapor transmission.

Various adhesive products were also used as the backing material instead of dry films. These adhesive products included: a non-woven film with an acrylic adhesive, a PET film coated with a synthetic rubber-resin adhesive, a polyethylene/EVA blend film coated with an acrylic adhesive; and, a polypropylene film with synthetic rubber. In all cases, the sensor was bonded extremely well to the tape at the adhesive interface to produce sensors through a film as illustrated in FIG. 4. Using PET tape as the backing material resulted in good bonding between the adhesive and sensor, as well as physical stiffness to enable the conductive resin to flow around and form the film-retaining feature.

Example 2: Performance Testing of Sensors Injection Molded Through Films

Web injection molded sensors produced in accordance with Example 1 were tested to assess the capability of the process to produce acceptable electrodes. 240 samples were produced having different backing materials and injection permutations. The contact face of each sensor was coated with a silver/silver chloride screen printable ink (DuPont grade 5880) and cured per manufacturer's specification.

Table 1 shows data collected for all sensors molded through PET and polypropylene webs. Table 1 shows the electrical resistance of the sensors. The values for electrical resistance were measured by clipping a standard lead wire connector to the post end, and placing a lead to measure in a line contact across the contact face of the sensor. The column labelled face resistance is the value of resistance over several points of the contact face but not in contact with the gate location. When the lead is placed in contact with the gate location, the resistance is significantly less due to the contact with exposed carbon fibers aligned perpendicular to the contact face. This demonstrates the exposed gate location, once covered up by the conductive silver ink, may be an advantage for electrical conduction. In all, Table 1 demonstrates that the present process is capable of producing commercially suitable sensors.

TABLE 1

Conductivity of sensors injection molded through PET or PP films.

|  | Face resistance (Ohm) | Gate resistance (Ohm) |
| --- | --- | --- |
| PET Avg. | 217 | 56 |
| PP Avg. | 195 | 65 |

Because the sensors produced are one-piece sensors, there is no need for a snap fit stud to retain the sensor on the web. A concern with electrodes comprising such one-piece sensors is how well the sensor adheres to the backing. As mentioned above, the PET web did not thermally bond well to the molded sensor, but polypropylene web did thermally bond well to the sensor. Ten samples comprising polypropylene web were tested to determine how much force was needed to pull the sensor through the web or break the sensor. Different resin temperature samples were used to see if better bonding between the web and the sensor resulted in a larger force. Table 2 shows that sensors produced using higher temperature resin have very high force, higher than the 10 lbf average of two-piece snap sensors produced by the prior art method. The large difference in stud pull values between the two resin temperatures leads to the hypothesis that it is not only the strength of the sensor and backing separately, but the bond between them that has a large influence on the force. The resin temperature made no difference to other parameters like conductivity or physical dimensions.

No numerical values were collected for the force needed to dislodge the sensor by pushing on it from the post side. However, a qualitative test was conducted by applying the lead wire snap to the sensor post while the sensor is unsupported from below. Every time the lead wire was attached, the sensor remained fixed to the film with no de-lamination visible. This would be the maximum force the sensor would be subjected to, and is a worst case scenario since it will generally be supported either on the liner or on the patient when the lead wire is attached in clinical applications.

TABLE 2

Stud pull force for sensors injection molded through polypropylene film.

| Resin Temperature (° F.) | Stud pull force (lbf) |
| --- | --- |
| 450 | 8 |
| 500 | 14 |
| Snap reference | 10 |

Example 3: Preparation and Performance Testing of ECG Electrodes

Multiple sensors were molded through polypropylene webs for actual electrode testing. The sensors were coated with a silver/silver chloride screen printable ink commercially available from DuPont (grade 5880). The polypropylene web with sensor molded into it was bonded to a pre-punched foam backing centered over a gel well. UV curable electrolyte gel was added to the foam well on top of the web injection molded sensor and cured. The electrodes were placed on a paper liner and aged at 49° C. inside a moisture proof bag in an oven for 2 days. The electrodes were taken out of the oven and out of the bag and placed in ambient lab conditions. Ten electrodes were tested at weekly intervals to determine the electrodes 'out of bag' performance.

The main measure of how well the sensor/web seal worked is in the electrical performance of the electrodes when left in an unsealed bag at ambient conditions for an 'out of bag (OOB)' time period. Table 3 shows the average performance of 10 electrodes at each interval out of bag (OOB). Testing was performed as per ANSI/AAMI EC12: 2000 method TS-667. Desired performance limits are: DC Offset (DCO)=100 mV, AC Impedance (ACZ)=3000 Ohm, Simulated Defibrillation Recovery (SDR)=100 mV, Slope=1. Up to 28 days there is no large difference in the performance, which confirms the assumption that the sensor/web seal is very good. In addition, ACZ2 values are lower than expected for the type of electrode, which highlights that the present electrodes have better sensitivity immediately after a defibrillation event than current commercial electrodes.

TABLE 3

Summary of the electrical results of 10 electrodes tested at each interval out of bag.

| Day OOB | DCO (mV) | ACZ1 (Ohm) | SDR (mV/s) | Slope | ACZ2 (Ohm) |
| --- | --- | --- | --- | --- | --- |
| 0 | 0.8 | 410 | 4.3 | 0.2 | 116 |
| 7 | 0.6 | 406 | 4.9 | 0.2 | 125 |
| 14 | 1.7 | 423 | 4.8 | 0.2 | 121 |
| 22 | 0.9 | 438 | 4.2 | 0.2 | 122 |
| 28 | 1.9 | 434 | 6.1 | 0.3 | 185 |

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. A process for producing a sensor for a biomedical electrode, comprising: injection molding an electrically conductive resin through a film of a backing material at a resin temperature range of 230-275 degrees Celsius to form the sensor directly in and thermally bonded to the backing material, the sensor comprising a contact face disposed on a first side of the film and a post protruding from a second side of the film opposite the first side; and, coating the contact face with a non-polarizable conductive material, wherein the backing material comprises polyethylene terephthalate or polypropylene.

2. A process for producing a biomedical electrode, comprising:

forming a sensor directly in a backing material by injection molding an electrically conductive resin through a film of the backing material at a resin temperature range of 230-275 degrees Celsius to form a thermal bond between the sensor and the backing, the sensor comprising a contact face disposed on a first side of the film and a post protruding from a second side of the film opposite the first side, wherein the backing material comprises polyethylene terephthalate or polypropylene;

coating the contact face with a non-polarizable conductive material;

applying an electrolyte over the non-polarizable conductive material coated on the contact face; and, applying a liner over the electrolyte.

3. The process according to claim 2, wherein the backing material secures the sensor in the film when the conductive resin is injection molded through the film.

4. The process according to claim 3, wherein securing the sensor in the film comprises adhering the conductive resin of the sensor to an adhesive coated on the film.

5. The process according to claim 2, wherein forming the sensor directly in the backing material comprises injection molding a plurality of sensors in a single film to form a web of the sensors in the single film.

6. The process according to claim 2, wherein the sensor comprises a flange disposed on the first side of the film, the contact face is a surface of the flange facing outwardly from the film, and the sensor is coated with the non-polarizable conductive material only on the contact face.

7. The process according to claim 2, wherein the backing material is a solid foam.

8. The process according to claim 2, wherein the conductive resin comprises a thermoplastic polymer matrix having conductive particles dispersed therein.

9. The process according to claim 2, wherein sensor comprises an integrally formed film-retaining feature.

10. The process according to claim 9, wherein the backing material comprises polyethylene terephthalate.

11. The process according to claim 10, further comprising: processing the backing material to reduce water vapor transmission between the film and the sensor.

12. The process according to claim 11, wherein the backing material comprises polyethylene terephthalate film with a polypropylene layer disposed on the first side.

13. The process according to claim 1, wherein the resin comprises polypropylene.

14. The process according to claim 13, wherein the backing material comprises polypropylene, wherein the sensor does not have a film-retaining feature.

15. The process according to claim 14, wherein the conductive resin is injected at a resin temperature of 500 degrees Fahrenheit.

16. The process according to claim 13, the backing material comprises polyethylene terephthalate film with a polypropylene layer disposed on the first side.

17. The process according to claim 2, wherein the resin comprises polypropylene, wherein the conductive resin is injected at a resin temperature of 500 degrees Fahrenheit.

18. The process according to claim 17, wherein the backing material is a polypropylene film, wherein the sensor does not have a film-retaining feature.

* * * * *

UNITED STATES PATENT AND TRADEMARK OFFICE
CERTIFICATE OF CORRECTION

PATENT NO.         : 10,800,079 B2
APPLICATION NO.    : 16/063559
DATED              : October 13, 2020
INVENTOR(S)        : Cam Derry Page 1 of 1

It is certified that error appears in the above-identified patent and that said Letters Patent is hereby corrected as shown below:

On the Title Page

Item [22], Column 1
Delete "Dec. 29, 2016" and insert -- Nov. 29, 2016 --, therefor.

Page 2, item [56], Column 2
Line 7, Delete "web.archive org" and insert -- web.archive.org --, therefor.
Line 8, Delete "en.wikipediaorg" and insert -- en.wikipedia.org --, therefor.

In the Claims

Column 16
Line 24, Claim 16, after "13," insert -- wherein --.

Signed and Sealed this
Twenty-ninth Day of December, 2020

Andrei Iancu
*Director of the United States Patent and Trademark Office*